(12) United States Patent
Bugdahn et al.

(10) Patent No.: US 12,049,441 B2
(45) Date of Patent: Jul. 30, 2024

(54) PROCESS FOR PREPARING LIMONENE AND COMPOSITION CONTAINING LIMONENE

(71) Applicant: SYMRISE AG, Holzminden (DE)

(72) Inventors: Nikolas Bugdahn, Holzminden (DE); Angela Köckritz, Berlin (DE); Elka Kraleva, Rostock (DE); Reinhard Eckelt, Rostock (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 17/799,506

(22) PCT Filed: Feb. 18, 2020

(86) PCT No.: PCT/EP2020/054233
§ 371 (c)(1),
(2) Date: Aug. 12, 2022

(87) PCT Pub. No.: WO2021/164852
PCT Pub. Date: Aug. 26, 2021

(65) Prior Publication Data
US 2023/0144944 A1 May 11, 2023

(51) Int. Cl.
*C07C 5/31* (2006.01)
*B01J 29/70* (2006.01)

(52) U.S. Cl.
CPC ............. *C07C 5/31* (2013.01); *B01J 29/7038* (2013.01); *C07C 2529/70* (2013.01)

(58) Field of Classification Search
CPC ... C07C 5/31; C07C 2529/70; C07C 2601/16; B01J 29/084; B01J 29/7038
See application file for complete search history.

(56) References Cited

U.S. PATENT DOCUMENTS

| | | | |
|---|---|---|---|
| 3,270,075 A | 8/1966 | Derfer | |
| 3,780,124 A | 12/1973 | Davis | |
| 3,780,125 A | 12/1973 | Takacs | |
| 4,508,930 A | 4/1985 | Wideman et al. | |

FOREIGN PATENT DOCUMENTS

| | | |
|---|---|---|
| CN | 104496741 A | 4/2015 |
| CN | 102126904 B | 7/2020 |
| WO | 2021164852 A1 | 8/2021 |

OTHER PUBLICATIONS

Search Report & Written Opinion; PCT/EP2020/054233, mailed Feb. 18, 2020, 11 pages.
Foletto, E.L. et al., "Gas-Phase B-Phinene Isomerization Over Acid-Activated Bentonite", Latin American Applied Research, 2002, vol. 32, pp. 141-144.
Ma, Xuetao et al., "Highly selective isomerization of biomass B-pinene over hierarchically acidic MCM-22 catalyst", Microporous and Mesoporous Materials, 2017, vol. 237, pp. 180-188.
Wikipedia, "Trickle-bed reactor", Mar. 23, 2018, 2 pages.

*Primary Examiner* — Thuan D Dang
(74) *Attorney, Agent, or Firm* — Timothy H. Van Dyke; WOLTER, VAN DYKE, DAVIS, PLLC

(57) ABSTRACT

What is proposed is a continuous process for producing limonene which has the feature that beta-pinene or beta-pinene-containing starting materials are isomerized in a trickle-bed reactor in the presence of acid catalysts.

13 Claims, 2 Drawing Sheets

PROCESS FOR PREPARING LIMONENE AND COMPOSITION CONTAINING LIMONENE

FIELD OF THE INVENTION

The present invention is in the field of terpene compounds and relates to a process for catalytic rearrangement of beta-pinene to limonene.

TECHNOLOGICAL BACKGROUND

Limonene is a natural substance from the group of monocyclic terpenes, which occurs in two enantiomers

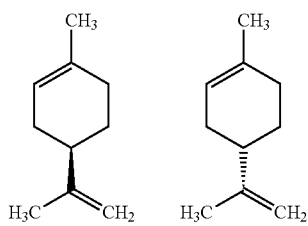

(R)-(+)-limonene (also referred to as D-(+)-limonene or (+)-limonene for short) and (S)-(−)-limonene (also referred to as L-(−)-limonene or (−)-limonene for short). The racemate of the two enantiomers is also known as dipentene.

Limonene is the most common monoterpene found in plants. (R)-(+)-Limonene is present especially in bitter orange peel oil, caraway oil, dill oil, coriander oil, lemon oil (about 65%) and orange oil (usually >90%). It has an orange-like fragrance. By contrast, (S)-(−)-limonene is present in noble fir and peppermint oil and smells of turpentine. Racemic limonene occurs inter alia in pine oil, Siberian pine needle oil, neroli oil, nutmeg oil and camphor oil.

The biosynthesis of limonene proceeds from geranyl pyrophosphate (GPP).

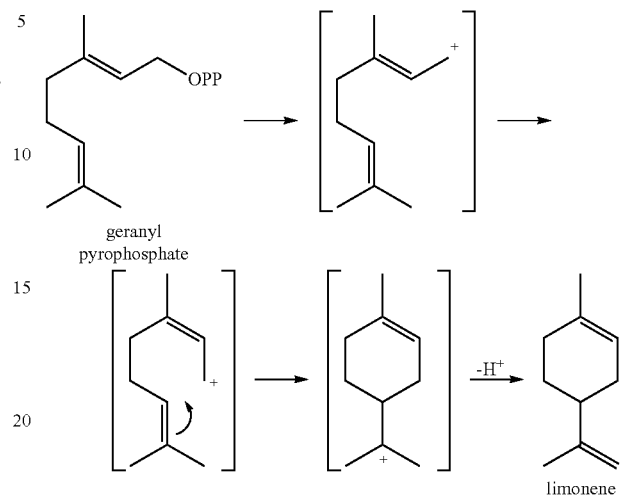

Limonene is an essential raw material for the fragrance industry and a starting material for a multiplicity of applications and products. It has in particular recently also been used as a "green" solvent and represents an alternative to the environmentally questionable BTX solvents.

While beta-pinene is a readily available source for the production of limonene, the difficulty in the acid-catalyzed isomerization of β-pinene is the potential for forming a broad product spectrum of bi-, tri-, and monocyclic terpenes via a series of equilibrium reactions that must be avoided to achieve high limonene selectivity. A selection from this possible product range is shown below.

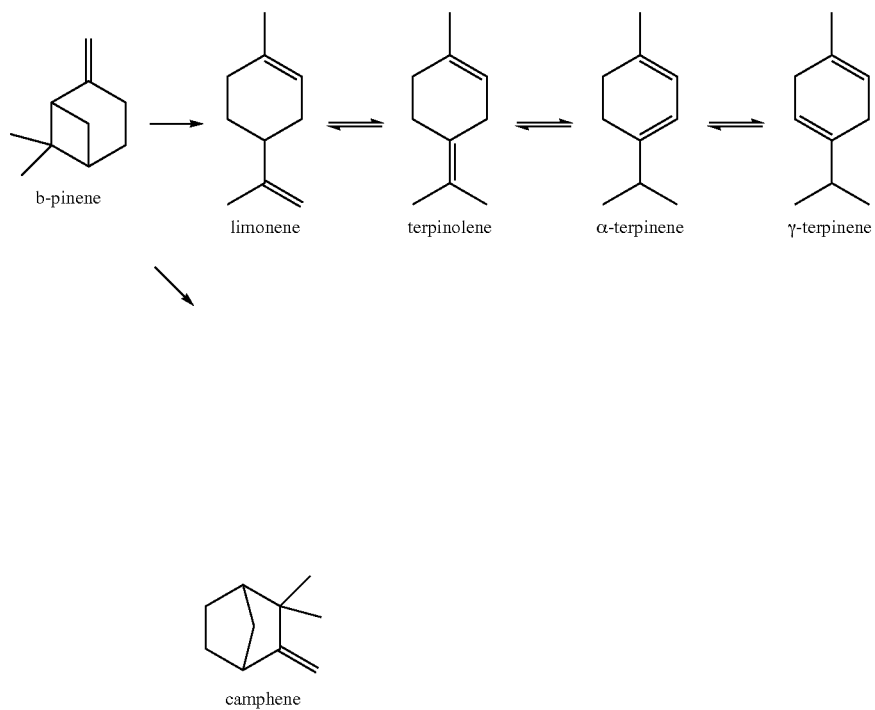

RELEVANT PRIOR ART

The first relevant publications include the two property rights U.S. Pat. No. 3,780,124 (DAVIS) and U.S. Pat. No. 3,780,125 (TAKACS) from 1973, which propose applying iodine to zeolites for the rearrangement of alpha-pinene.

U.S. Pat. No. 4,508,930 (WIDEMANN) discloses the rearrangement of terpenes into limonene in the presence of supported alkali metal sulfide catalysts at high temperatures.

The isomerization of pinene to limonene and other byproducts in the presence of zeolites is already known from U.S. Pat. No. 3,270,075 (GLIDDEN). The reaction takes place in the liquid phase at 65° ° C. to 110° C. The catalyst is generally described as $Me_x/n[(AlO_2)_x(SiO_2)_y]*_zH_2O$ and specific mention is made of:

$Na_{86}[(AlO_2)_{86}(SiO_2)_{106}]*267\ H_2O$.

The two Dalian University Chinese patents CN 102126904B and CN 102343277B likewise describe the isomerization of pinenes to limonene in the presence of heterogeneous acid catalysts. The catalysts employed are acidic molecular sieves which have been aftertreated with halides and with bases.

Reference is also made to the two papers of Ma et.al. in MICROPOROUS AND MESOPOROUS MATERIAL 237, pp. 180-188 (2017) and Golets et al. in CHEM. REV. 115, S. 3141-3196 (2017).

The disadvantage is that the processes known from the prior art do not represent economically viable alternatives either in terms of yields or selectivities. The processes generally also operate at very high temperatures, require the use of toxic solvents, cannot be performed on a continuous basis and also exhibit insufficient catalyst service lives. In addition, the reaction products often contain unwanted byproducts such as especially terpinenes in amounts that adversely affect product quality.

SUMMARY

It is therefore a first object of the present invention to provide a process for continuous isomerization of beta-pinene to limonene which has yields and selectivities of at least 65%, preferably at least 75%, and affords very largely (i.e. about 15% to 20% by weight) only camphene as a byproduct. The limonene should be obtained specifically (>90% by weight) as the L isomer.

It is a further object of the invention to run the process such that it is possible to eschew, completely if possible or at least partially, the use of toxic solvents, especially from the BTX series. The reaction should also be performable below 100° C. and the catalyst should have a service life that is sufficiently long to allow it to be used and recovered several times without workup.

DESCRIPTION OF THE INVENTION

The present invention firstly provides a continuous process for producing limonene which has the feature that beta-pinene or beta-pinene-containing starting materials are isomerized in a trickle-bed reactor in the presence of acid catalysts.

What is claimed specifically is a process comprising or consisting of the steps of:
(a) providing beta-pinene or a beta-pinene-containing starting material;
(b) providing a trickle bed reactor with a catalyst fixed bed;
(c) filling the reactor fixed bed with a heterogeneous acid catalyst;
(d) applying the starting material at the top of the reactor and passing the starting material over the catalyst fixed bed;
(e) withdrawing the limonene or a limonene-enriched fraction at the reactor outlet.

It has surprisingly been found that performing the process using a trickle bed reactor with an integrated fixed catalyst bed make it possible to achieve continuous isomerization of beta-pinene to limonene with selectivities of more than 65%. The process management in the fluidized bed reactor allows kinetic control of the selectivity via establishment of an optimal residence time in the catalyst bed. This avoids establishment of equilibria which, for example in a batch process, leads to formation of thermodynamically more stable but undesired isomers. This also makes it possible to largely avoid consecutive reactions to afford oligomeric or even polymeric byproducts which would otherwise result in premature deactivation of the catalyst. Compared to conventional fixed-bed reactors the fluidized bed reactor altogether achieves higher catalyst service lives.

It is noted that beta-pinene can exist in two enantiomeric forms, namely (S,S) and (R,R). Thus in the context of the present invention the term "beta-pinene" is to be understood as comprehending both forms or mixtures thereof. The preferred starting material is (1S, 5S) beta-pinene, also referred to as (−)-beta-pinene. Meanwhile, (1R, 5R)-beta-pinene, also referred to as (+)-beta-pinene, is particularly preferred since this allows enantiomerically pure D-limonene to be obtained.

Catalysts

According to the invention the isomerization is carried out in the presence of solid acids; the heterogeneous catalysts employed are preferably Brönsted or Lewis acids. Especially suitable for this purpose are zeolites, especially those selected from the group consisting of the Y, H-Beta, ZSM-5 and MMW types. MWW zeolites of the MCM-22 or PSH-3 type are particularly preferred.

Figure 2:
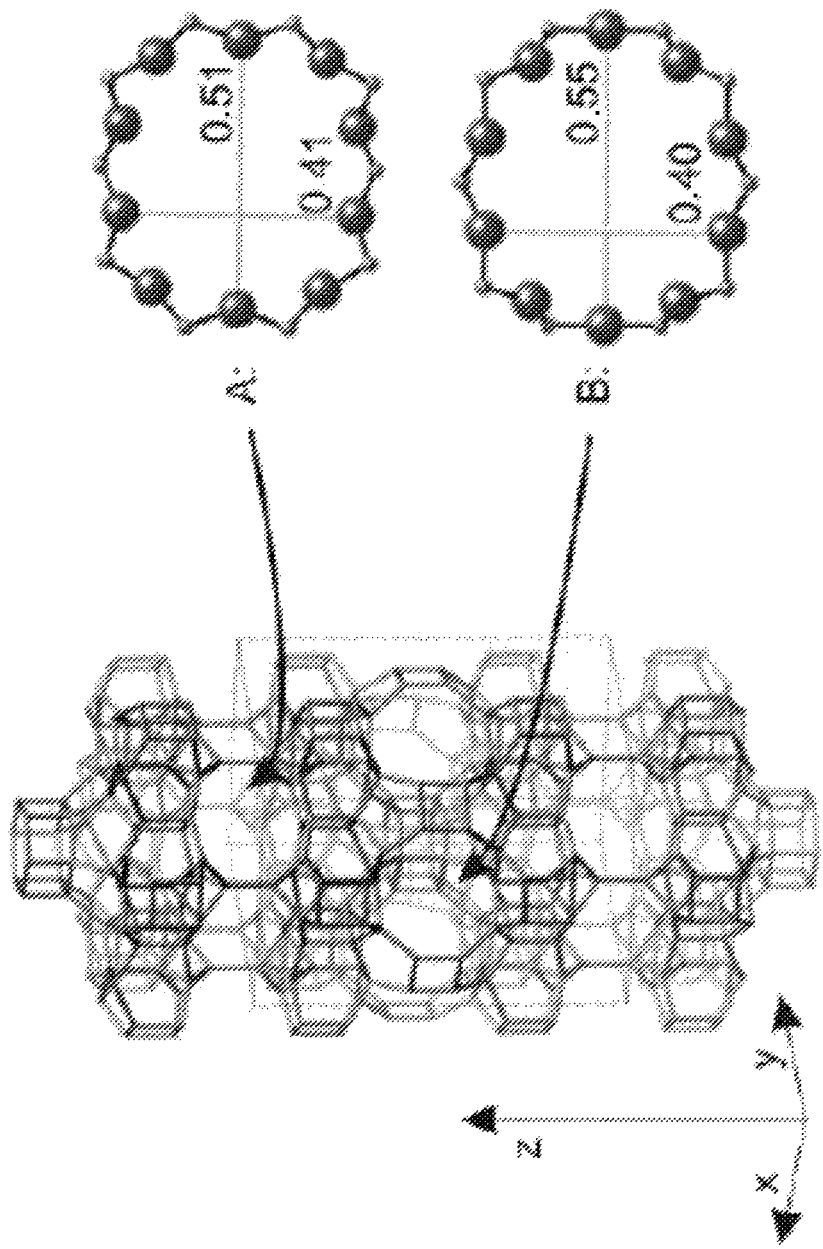
FIG. 2 shows a diagram of MWW zeolite.

The term "MWW" is understood as referring to a zeolite type as reproduced in FIG. 2:

MWW zeolites consist of two ten-ring pore systems that are separate from one another. A distinction is made between variants A and B, where the cavities are linked linearly and sinusoidally respectively.

It is preferable to employ MWW zeolites which have previously been calcined and/or activated by acids. Particularly preferred zeolites are MCM-22 or PSH-3 type zeolites which conform to the formula

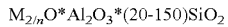

$M_{2/n}O*Al_2O_3*(20-150)SiO_2$ and are known for example from EP 0064205 B1 (BAYER). It is preferable to subject the MMW zeolites to calcining and/or activation by acid treatment before use.

The calcining may preferably be performed over a period of about 1 to about 10 hours and preferably 4 to 6 hours at a temperature of about 400° ° C. to about 1000° C. and in particular 400° ° C. to 600° C., nitric acid being particularly suitable for the acid activation. MCM-22 zeolites which have been previously calcined and activated with nitric acid are very particularly preferred.

Trickle Bed Reactor and Reaction Management

Trickle bed reactors are essentially known from wastewater treatment. In the process according to the invention too, the starting material is introduced at the top of the reactor and then trickles through the catalytic fixed bed in which the isomerization takes place. It has further proven advantageous to carry out the reaction in the presence of an inert gas, specifically nitrogen, which is run in cocurrent but preferably in countercurrent, since this makes it possible to avoid oxidative decomposition reactions and increases catalyst service life.

The process according to the invention may be performed with or without a solvent. However, the use of a solvent increases selectivity and improves catalyst service life and is therefore preferred. Suitable solvents are aprotic solvents such as $C_6$-$C_8$-alkanes, in particular heptane, 1,4-dioxane or $C_1$-$C_4$-alkyl acetates, especially ethyl acetate. The mass ratio of solvent to β-pinene is preferably between 90:10 and 50:50, a ratio of about 80:20 being preferred.

It has proven possible and advantageous to perform the process under mild conditions, namely at a temperature in the range from 50° C. to 120° C. and in particular at about 70° ° C. to 80° C. and at a pressure in the range from 1 to 10 bar and in particular at about 2 to 4 bar.

Solvent Preparation

The present invention further provides a solvent composition obtainable or obtained by the present process, consisting of
(a) about 70% to about 80% by weight of limonene and
(b) about 15% to about 20% by weight of camphene with the proviso that the reported amounts sum to 100% by weight optionally with pinenes, terpinenes and terpinolenes.

INDUSTRIAL APPLICABILITY

The present invention finally also provides for the use of a MMC-22 zeolite, optionally after preceding calcining and/or acid activation, as catalyst for rearrangement of beta-pinene into limonene in a process as elucidated above.

EXAMPLES

Examples 1 to 11

Continuous Isomerization of Beta-Pinene

A commercially available, continuous 1" flow-through reactor apparatus of 60 cm in length made of titanium (Parr Instruments) and fitted with a two-zone heating jacket and internal temperature sensors was utilized for the experiments The liquid feed and argon were metered into the reactor head via an HPLC pump and a mass flow controller respectively. Temperature, pressure and flows were monitored and adjusted via accompanying software. The granulated catalyst was filled into middle of the reactor tube. Free reactor volume above and below the catalyst bed was filled with inert corundum granules. 5 g of a solid acid catalyst (particle size 0.3-0.7 mm) were placed in the middle of the reactor between beds of corundum granules. 109.6 g of a commercial ß-pinene was dissolved in 400 g of solvent and pumped over the catalyst bed at the desired temperature using an HPLC pump. Simultaneously an argon stream was metered into the reactor at 50 ml/min at a pressure of 2 bar. After decompression of the product mixture, samples were taken at regular intervals downstream of the reactor outlet and subjected to analysis by off-line gas chromatography. Further experimental conditions for other examples are apparent from table 1. The zeolite Y catalysts were obtained from Zeolyst, the abbreviation TOS stands for time-on-stream.

Figure 1:
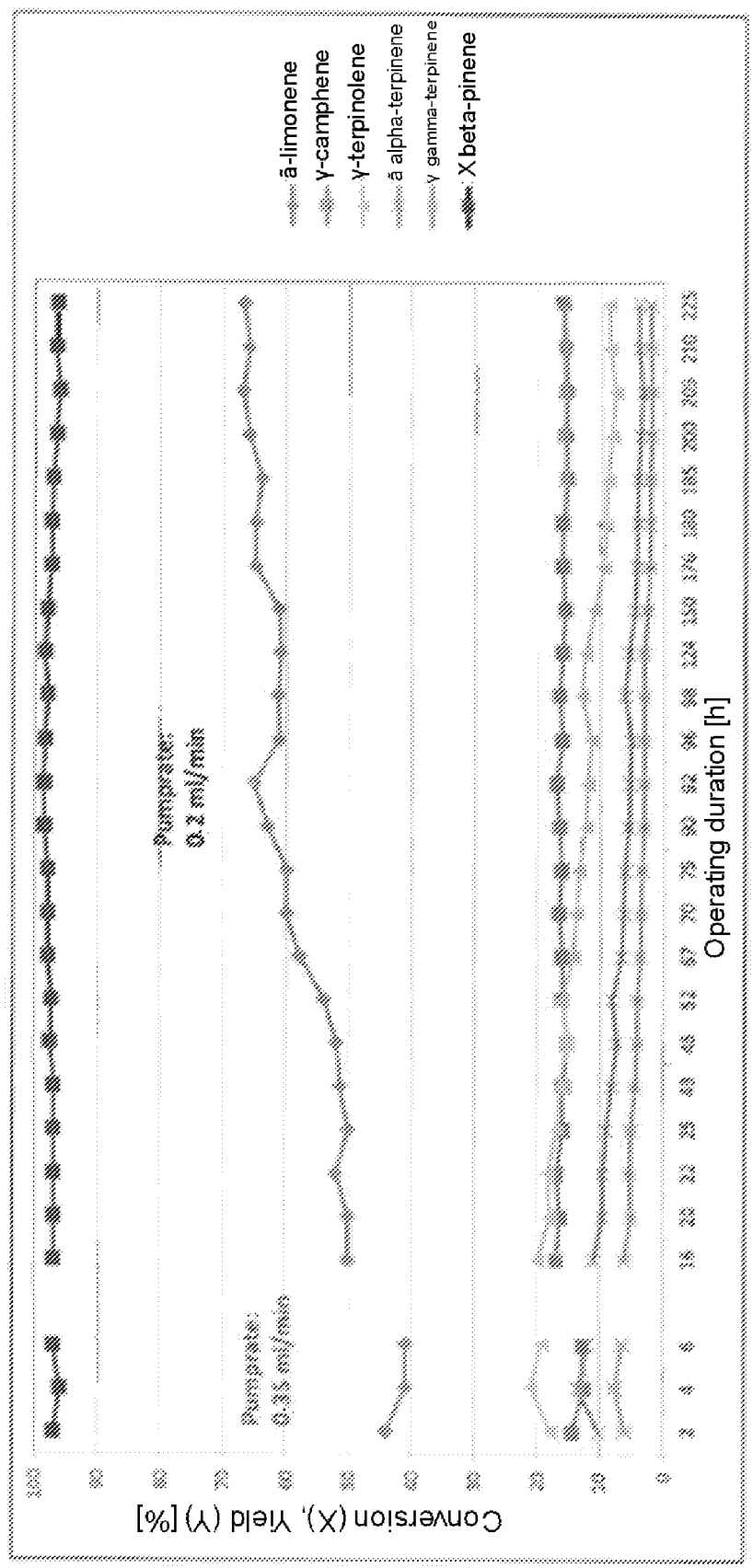
FIG. 1 shows a graph of a long-term test of the activity and selectivity of the MCM-22 catalyst monitored at two different pump rates over a total of 225 h. A limonene yield of 67% at 97% conversion was determined after 225 h.

It is also possible (example 10) to employ ß-pinene as the feed directly without a solvent. In a long-term test (example 11, FIG. 1) the activity and selectivity of the MCM-22 catalyst was monitored at two different pump rates (see FIG. 2) over a total of 225 h. A limonene yield of 67% at 97% conversion was determined after 225 h.

TABLE 1

Experimental results

| | β-Pinene | | Cat | Solv. | Pump rate | T | TOS | Conversion [%] | Yields [%] | | | | |
|---|---|---|---|---|---|---|---|---|---|---|---|---|---|
| Ex. | [g] | Catalyst | [g] | [g] | [ml/min] | [° C.] | [h] | β-Pinene | Limonene | Terpinolene | Camphene | α-Terpinene | γ-Terpinen |
| 1 | 54.8 | Zeolite Y (CNV 100) | 5 | Heptane (200) | 0.5 | 90 | 8 | 93.0 | 54.0 | 17.8 | 21.0 | 8.7 | 5.1 |
| 2 | 54.8 | Zeolite Y (CBV DE10) | 5 | Heptane (200) | 0.5 | 90 | 6 | 96.4 | 32.6 | 16.5 | 10.3 | 23.0 | 11.0 |
| | | | 5 | Heptane (200) | 0.5 | 78 | 8 | 90 | 28.6 | 13.5 | 29.4 | 8.8 | 4.4 |
| 3 | 54.8 | Zeolite Y (CBV 712) | 5 | Heptane (200) | | 78 | 8 | 96.0 | 6.0 | 9.4 | 40.0 | 12.0 | 7.0 |
| 4 | 54.8 | MCM-22 | 5 | Heptane (200) | 1.5 | 75 | 3 | 79.0 | 30.0 | 9.0 | 23.3 | 7.0 | 3.0 |
| 5 | 54.8 | $ZrO_2/SiO_2$ | 5 | 1,4-Dioxane (200) | 0.5 | 75 | 2 | 93.0 | 32.0 | 18.0 | 16.0 | 15.0 | 8.0 |
| 6 | 109.6 | MCM-22 | 3 | 1,4-Dioxane (200) | 0.5 | 73 | 8 | 97.0 | 51.0 | 15.6 | 16.4 | 8.8 | 4.5 |
| 7 | 109.6 | MCM-22 | 3 | 1,4-Dioxane (200) | 0.35 | 73 | 20 | 98.0 | 66.0 | 9.4 | 17.5 | 4.1 | 2.3 |
| 8 | 109.6 | MCM-22 | 3 | 1,4-Dioxane (200) | 0.2 | 73 | 50 | 97.0 | 71.0 | 8.8 | 17.0 | 4.0 | 2.1 |

TABLE 1-continued

Experimental results

| Ex. | β-Pinene [g] | Catalyst | Cat [g] | Solv. [g] | Pump rate [ml/min] | T [° C.] | TOS [h] | Conversion [%] β-Pinene | Yields [%] Limonene | Terpinolene | Camphene | α-Terpinene | γ-Terpinen |
|---|---|---|---|---|---|---|---|---|---|---|---|---|---|
| 9 | 109.6 | MCM-22 | 3 | 1,4-Dioxane (200) | 0.2 | 73 | 50 | 97 | 71.0 | 8.8 | 17.0 | 4.0 | 2.1 |
| 10 | Pure | MCM-22 | 5 | — | 0.2 | 73 | 2 | 96.0 | 64.0 | 14.3 | 8.0 | 3.4 | 1.8 |
| 11 | 109.6 | MCM-22 | 5 | 1,4-Dioxane (200) | 0.2 | 73 | 225 | 97.0 | 67.0 | 8.7 | 16.0 | 4.0 | 2.0 |

The invention claimed is:

1. A process for producing limonene, wherein the process comprises isomerizing beta-pinene or beta-pinene-containing starting materials in a trickle-bed reactor in the presence of at least one acid catalyst and an inert gas.

2. The process as claimed in claim 1, comprising or consisting of the steps of:
   (a) providing beta-pinene or a beta-pinene-containing starting material;
   (b) providing a trickle bed reactor with a catalyst fixed bed;
   (c) filling the reactor fixed bed with a heterogeneous acid catalyst;
   (d) applying the starting material at the top of the reactor and passing the starting material over the catalyst fixed bed;
   (e) withdrawing the limonene or a limonene-enriched fraction at the reactor outlet.

3. The process as claimed in claim 2, wherein the heterogeneous catalyst is a Brönsted or Lewis acids.

4. The process as claimed in claim 1, wherein the at least one catalyst is a zeolite.

5. The process as claimed in claim 4, wherein the zeolite is selected from the group consisting of the Y, H-Beta, ZSM-5 and MMW types.

6. The process as claimed in claim 5, wherein the MWW zeolite employed is an MCM-22 or PSH-3 zeolite.

7. The process as claimed in claim 4, wherein the zeolite has previously been calcined and/or activated by an acid.

8. The process as claimed in claim 5, wherein the zeolite comprises MCM-22 zeolite which has been previously calcined and activated with nitric acid.

9. The process as claimed in claim 1, wherein isomerizing is performed in the presence of an aprotic solvent.

10. The process as claimed in claim 9, wherein the aproteic solvent is selected from $C_6$-$C_8$-alkanes, 1,4-dioxane or $C_1$-$C_4$-alkyl acetates.

11. The process as claimed in claim 9, wherein the beta-pinene and the aprotic solvent are employed in a weight ratio of about 90:10 to 50:50.

12. The process as claimed in claim 1, wherein isomerizing is performed at a temperature in the range from 50° C. to 120° C.

13. The process as claimed in claim 1, wherein isomerizing is performed at a pressure in the range from 1 to 10 bar.

* * * * *